United States Patent
Petit

(10) Patent No.: US 10,232,127 B2
(45) Date of Patent: Mar. 19, 2019

(54) CANNULA FOR A DEVICE FOR DISPENSING A FLUID PRODUCT

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 15/528,550

(22) PCT Filed: Dec. 16, 2015

(86) PCT No.: PCT/FR2015/053546
§ 371 (c)(1),
(2) Date: May 22, 2017

(87) PCT Pub. No.: WO2016/097605
PCT Pub. Date: Jun. 23, 2016

(65) Prior Publication Data
US 2017/0259285 A1 Sep. 14, 2017

(30) Foreign Application Priority Data

Dec. 16, 2014 (FR) .................................... 14 62489

(51) Int. Cl.
*B21G 1/08* (2006.01)
*A61M 5/32* (2006.01)
(Continued)

(52) U.S. Cl.
CPC ...... *A61M 5/3286* (2013.01); *A61M 5/31591* (2013.01); *A61M 5/31593* (2013.01);
(Continued)

(58) Field of Classification Search
CPC .................. B05B 11/0008; A61M 5/31591
(Continued)

(56) References Cited

U.S. PATENT DOCUMENTS 5,064,411 A * 11/1991 Gordon, III ........... A61B 42/10
128/846
5,307,953 A * 5/1994 Regan ............... A61M 15/0028
222/82
(Continued)

FOREIGN PATENT DOCUMENTS

DE 44 12 041 A1 10/1995
DE 102 24 101 A1 12/2003
(Continued)

OTHER PUBLICATIONS

International Search Report of PCT/FR2015/053546 dated Mar. 29, 2016.
(Continued)

*Primary Examiner* — Vishal Pancholi
(74) *Attorney, Agent, or Firm* — Sughrue Mion, PLLC

(57) ABSTRACT

A hollow cannula (4) including a perforating tip (5) for perforating a perforating site, said perforating tip (5) being provided with an opening (6), said opening (6) defining a peripheral edge (7) that extends around said opening (6) and that includes a distal axial end and a proximal axial end, said distal axial end of said peripheral edge (7) forming the distal axial end (59) of the perforating tip (5), said distal axial end (59) of the perforating tip (5) being arranged on the longitudinal central axis (A) of said cannula (4), said perforating tip (5) having an outer shape that is rounded in the radial direction, and said distal axial end (59) of said perforating tip (5) being of shape that is rounded in the axial direction.

9 Claims, 3 Drawing Sheets

(51) Int. Cl.
*B05B 11/02* (2006.01)
*A61M 5/315* (2006.01)
*B05B 11/00* (2006.01)

(52) U.S. Cl.
CPC .......... *B05B 11/0008* (2013.01); *B05B 11/02* (2013.01); *B05B 11/025* (2013.01); *B21G 1/08* (2013.01); *A61M 5/32* (2013.01); *A61M 2205/195* (2013.01)

(58) Field of Classification Search
USPC ....... 222/82, 83, 83.5, 321.6, 326, 327, 386; 604/272–274
See application file for complete search history.

(56) References Cited

U.S. PATENT DOCUMENTS

| | | | | |
|---|---|---|---|---|
| 5,669,543 | A * | 9/1997 | Ueno | B65C 7/003 112/222 |
| 5,813,570 | A * | 9/1998 | Fuchs | B05B 11/02 222/153.06 |
| 5,868,721 | A * | 2/1999 | Marinacci | A61M 5/2033 604/239 |
| 6,626,379 | B1 * | 9/2003 | Ritsche | B05B 11/0078 239/303 |
| 6,708,846 | B1 * | 3/2004 | Fuchs | A61M 11/06 222/327 |
| 6,979,318 | B1 | 12/2005 | McDonald et al. | |
| 7,299,949 | B2 * | 11/2007 | Greiner-Perth | B05B 11/02 222/153.13 |
| 2001/0044604 | A1 * | 11/2001 | Luther | A61M 25/0068 604/164.06 |
| 2003/0153879 | A1 | 8/2003 | Luther | |
| 2005/0029288 | A1 * | 2/2005 | Heldt | B05B 11/02 222/83 |
| 2006/0276759 | A1 * | 12/2006 | Kinast | A61M 5/3286 604/272 |
| 2009/0163877 | A1 | 6/2009 | Christoffersen et al. | |

FOREIGN PATENT DOCUMENTS

| | | |
|---|---|---|
| EP | 0 495 214 A1 | 7/1992 |
| EP | 0 546 607 A1 | 6/1993 |
| WO | 90/001349 A1 | 2/1990 |
| WO | 2004/064903 A1 | 8/2004 |

OTHER PUBLICATIONS

International Preliminary Report on Patentability with a Translation of Written Opinion issued from the International Bureau in counterpart International Application No. PCT/FR2015/053546, dated Aug. 10, 2017.

* cited by examiner

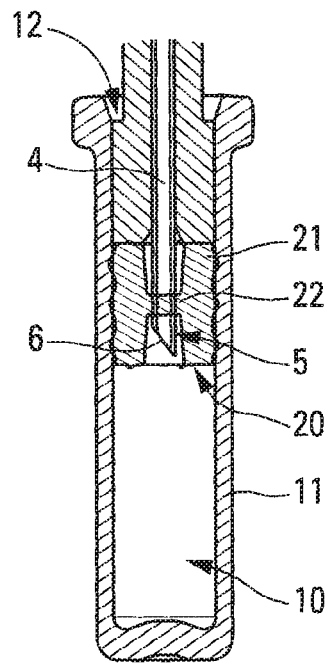
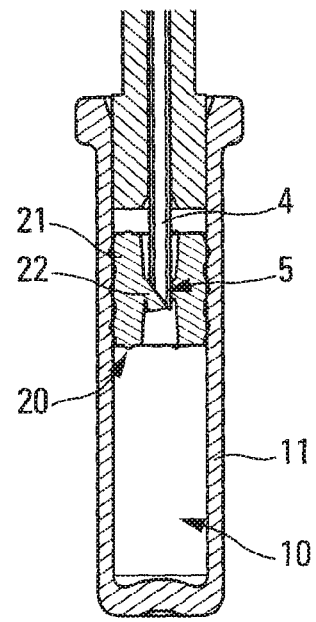
Fig. 2a  Fig. 2b
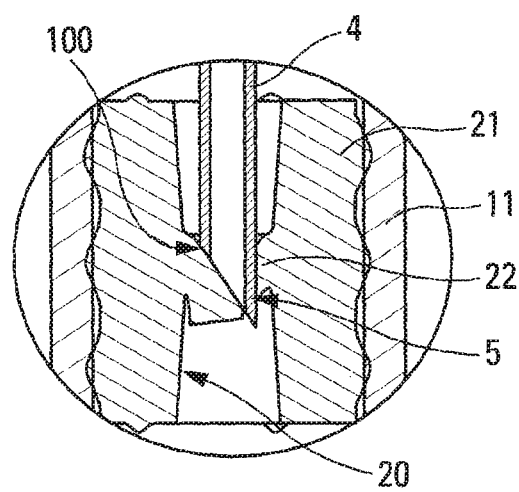
Fig. 2c

CANNULA FOR A DEVICE FOR DISPENSING A FLUID PRODUCT

CROSS REFERENCE TO RELATED APPLICATIONS

This application is a National Stage of International Application No. PCT/FR2015/053546 filed Dec. 16, 2015, claiming priority based on French Patent Application No. 1462489 filed Dec. 16, 2014, the contents of all of which are incorporated herein by reference in their entirety.

The present invention relates to a cannula and to a fluid dispenser device including such a cannula.

Fluid dispenser devices including a cannula are well known.

A first family of devices comprises injection devices that use said cannula as an injection needle for perforating an injection site on a patient's body.

A second family of devices comprises devices of the single-dose or two-dose type that are adapted to dispense one or two doses of fluid in a single actuation, in which the cannula is for perforating a stopper that forms an injection site. As can be seen in FIG. 1, the devices of the second family generally comprise a body 1 that receives a reservoir 10 containing one or two doses of fluid, and a dispenser head 2 that is provided with a dispenser orifice 3, and that is axially movable relative to said body 1 during actuation. The reservoir 10 is generally formed by a blind hollow tube 11 having an axial opening 12 that is proximal (relative to the dispenser orifice 3) and that is closed in leaktight manner by a stopper 20. The dispenser head 2 generally includes a cannula or needle 4 of generally cylindrical shape that is connected at one end to said dispenser orifice 3, and that is provided at its other end with a perforating tip 5 that is adapted to perforate said stopper 20 during actuation, the stopper 20 thus being moved in said reservoir 10 so as to expel the dose(s) of fluid through said cannula 4, towards said dispenser orifice 3. Document EP 0 546 607 describes a device of this type.

A drawback with the prior-art devices of the second family relates to the risk of leaks during actuation, which changes the dose dispensed and degrades metering reproducibility between various devices of the same type. In particular, as can be seen in FIG. 2a, the opening 6 in the perforating tip 5 of the cannula 4 is generally formed by a bevel at its axial end that is distal (relative to the dispenser orifice 3), thus forming a peripheral edge 7 of plane surface that surrounds said opening 6. In order to make it easier to perforate the stopper 20, the angle of said bevel is relatively sharp, such that the axial extent of said opening 6, i.e. the axial distance between the distal axial end and the proximal axial end of said peripheral edge 7, can be greater than the thickness of the wall 22 of the stopper 20 that is perforated by said cannula 4 at the beginning of actuation. This can thus lead to leaks while the stopper 20 is being perforated, with fluid potentially flowing out from the reservoir 10 without passing into said cannula 4. Furthermore, as can be seen in FIGS. 2b and 2c, with a standard cannula such as the cannula in FIG. 2a, there is the risk of deteriorating the hinge zone 100 close to the proximal axial end of said peripheral edge of the opening, generating potential leaks.

Documents DE 4 412 041, DE 102 24 101, and US 2009/163877 describe other prior-art devices.

An object of the present invention is to provide a cannula and a fluid dispenser device, in particular of the single-dose or two-dose type, that do not have the above-mentioned drawbacks.

Another object of the present invention is to provide a cannula and a fluid dispenser device, in particular of the single-dose or two-dose type, that improve metering accuracy and metering reproducibility for a plurality of devices of the same type, by limiting or eliminating the risk of leaks during actuation.

Another object of the present invention is to provide a cannula and a fluid dispenser device, in particular of the single-dose or two-dose type, that are simple and inexpensive to manufacture and to assemble.

The present thus provides a hollow cannula including a perforating tip for perforating a perforating site, said perforating tip being provided with an opening, said opening defining a peripheral edge that extends around said opening and that includes a distal axial end and a proximal axial end, said distal axial end of said peripheral edge forming the distal axial end of the perforating tip, said distal axial end of the perforating tip being arranged on the longitudinal central axis of said cannula, said perforating tip having an outer shape that is rounded in the radial direction, and said distal axial end of said perforating tip being of shape that is rounded in the axial direction.

Advantageously, said opening includes a distal portion of width that is small relative to the width of said cannula.

Advantageously, said peripheral edge includes a radial narrowing for defining said distal portion of small width of said opening.

Advantageously, said peripheral edge is curved axially.

Advantageously, said perforating tip is formed by stamping said cannula.

The present invention also provides a fluid dispenser device comprising a body, and a dispenser head that is provided with a dispenser orifice and that is axially movable relative to said body during actuation, said body receiving a reservoir containing fluid, said reservoir comprising a hollow tube having a proximal axial opening that is closed by a stopper that is adapted to slide in leaktight manner in said tube during actuation, said dispenser head including a hollow cannula as described above.

Advantageously, said cannula is connected at one end to said dispenser orifice, and it is provided at its other end with said perforating tip.

Advantageously, said reservoir is formed by a blind hollow tube.

Advantageously, said reservoir contains a single dose of fluid for dispensing during a single actuation of the device.

Advantageously, said reservoir contains a plurality of doses of fluid for dispensing during successive actuations of the device.

These characteristics and advantages and others appear more clearly from the following detailed description, given by way of non-limiting examples, and with reference to the accompanying drawings, and in which:

FIG. 2a is a section view of a detail of a standard device of the prior art;

FIGS. 2b and 2c are detailed views of the device shown in FIG. 2a, during perforation of the stopper;

The present invention relates more particularly to a device of the type disclosed in document EP 0 546 607.

However, it should be understood that the present invention is not limited to that type of device, but, on the contrary, applies to any type of fluid dispenser device including a cannula for perforating an injection site. The injection site may be a part of the user's or patient's body, in particular with injection devices, or a stopper that needs to be perforated before or at the beginning of actuation, in particular with devices of the single-dose or two-dose type, including a reservoir that is closed by such a stopper.

Figure 4:
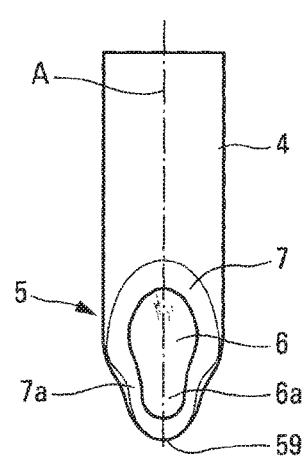
FIGS. 4 to 6 are views of a detail of the FIG. 3 cannula.
Figure 5:
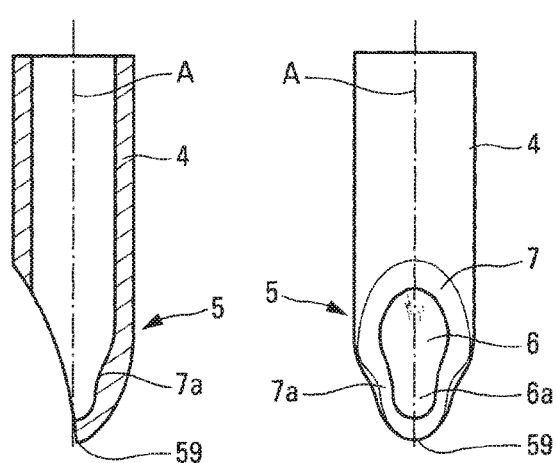

In the description, the terms "axial" and "radial" are relative in particular to the longitudinal central axis A of the cannula 4, as can be seen in FIGS. 4 and 5. The terms "proximal" and "distal" are relative to the dispenser orifice 3 formed in the dispenser head 2.

Figure 1:
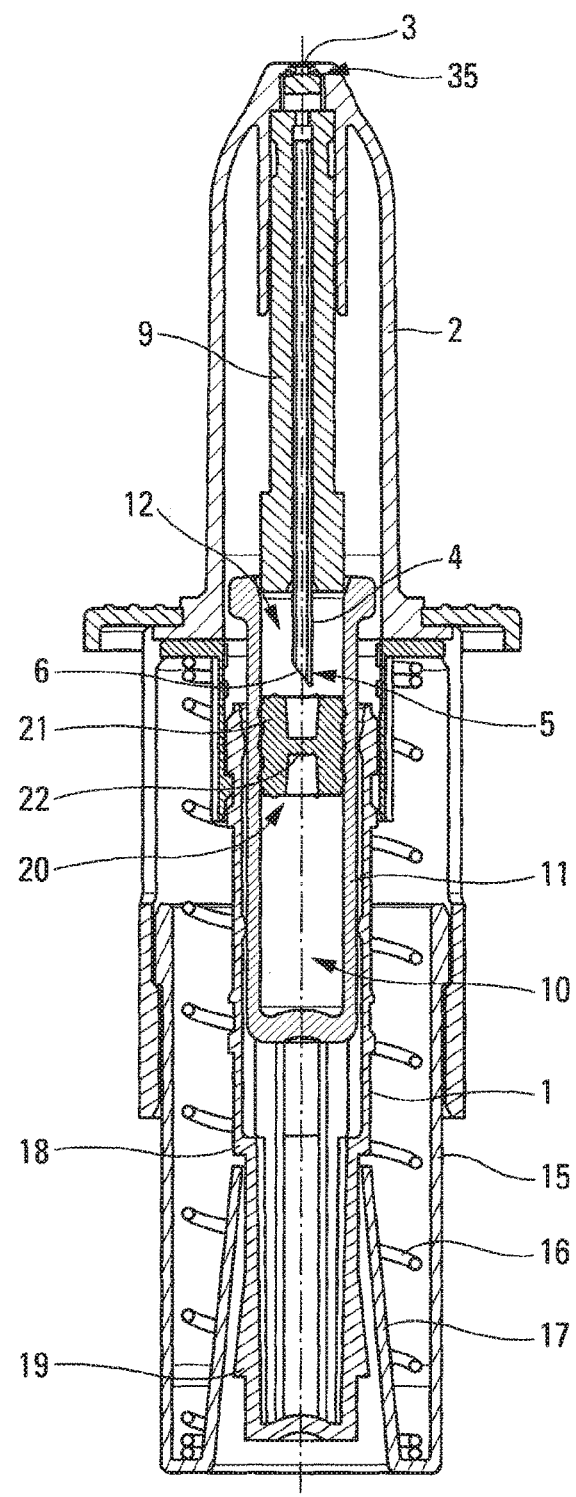
FIG. 1 is a diagrammatic view of a dispenser device of the two-dose type to which the present invention may be applied.

The invention applies in particular to devices of the single-dose or two-dose type as shown in FIG. 1. As described above, such a device includes a body 1 that receives a reservoir 10 containing one or two doses of fluid, and a dispenser head 2, provided with a dispenser orifice 3, is axially movable relative to said body 1 during actuation.

The reservoir 10 contains one or two doses of fluid. Advantageously, said reservoir 10 is formed by a blind hollow tube 11, e.g. made of glass, having a proximal axial opening 12 that is closed by a stopper 20, e.g. made of elastomer, that is adapted to slide in leaktight manner in said tube 11 during actuation. Said stopper 20 comprises both a tubular axial portion 21 that slides in leaktight manner in the tube 11, and also a transverse wall 22 for being perforated during actuation.

The dispenser head 2 generally includes a hollow cannula or needle 4 of generally cylindrical shape that is connected at one end to said dispenser orifice 3, and that is provided at its other end with a perforating tip 5 that is adapted to perforate said stopper 20 during actuation, the stopper 20 thus being moved in said reservoir 10 so as to expel the dose(s) of fluid through said cannula 4, towards said dispenser orifice 3. The cannula 4 may be inserted into a cannula support 9 that may itself be fastened in said dispenser head 2. Advantageously, a spray profile 35 may be formed directly upstream from the dispenser orifice 3, e.g. between the end wall of said dispenser head 2 and the proximal axial end of said cannula support 9.

The perforating tip 5 for perforating said stopper 20 is provided with an opening 6, said opening 6 defining a peripheral edge 7 that extends around said opening 6 and that includes a distal axial end and a proximal axial end.

An actuator member 15 connected to said body 1 may be provided to perform actuation. In the embodiment shown in FIG. 1, the actuator member 15 is urged towards its rest position by a spring 16, and is movable manually against the force of the spring 16 so as to move both the body 1 and the reservoir 10 relative to the dispenser head 2. Since the embodiment in FIG. 1 is a two-dose dispenser device, the actuator member includes dose-splitting means that, in this embodiment, are in the form of one or more flexible tabs 17 that co-operate with respective radial shoulders 18, 19 formed on said body 1. Thus, in order to dispense the first dose, the flexible tab 17 co-operates with the shoulder 18, then the spring 16 returns the actuator member 15 into its rest position in which said flexible tab co-operates with the second shoulder 19. Other dose-splitting means may be envisaged.

FIGS. 3 to 6 show an advantageous embodiment of the present invention.

In this embodiment, said distal axial end of said peripheral edge 7 forms the distal axial end 59 of the perforating tip 5, and said distal axial end 59 of the perforating tip 5 is arranged on the longitudinal central axis A of said cannula 4.

Advantageously, said opening 6 includes a distal portion 6a of width that is small relative to the width of said cannula 4, which distal portion may in particular be defined by a radial narrowing 7a of said peripheral edge 7.

The invention thus makes it possible to generate a section profile that is much smaller, in particular much narrower, than the outer width of the cannula 4, and this substantially improves the dynamic sealing of the cannula 4 with the stopper 20 during actuation. Furthermore, the perforating force is smaller, typically about 6 newtons (N).

Figure 6:
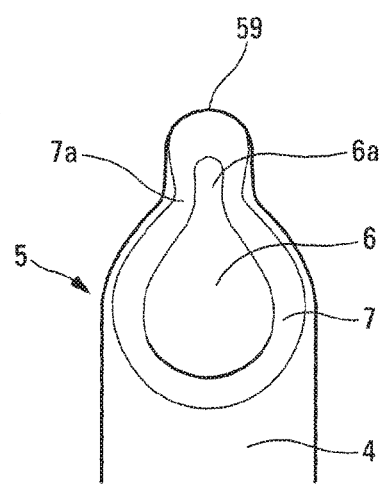

In this particular embodiment, the peripheral edge 7 that surrounds the opening 6 of the perforating tip is not plane in surface, but curved axially, as can be seen in FIG. 4. Advantageously, the peripheral edge does not include a projecting profile. The perforating head 5 advantageously has an outer shape that is rounded in the radial direction, as shown in the FIGS. 3 and 4. Furthermore, the distal axial end 59 of said perforating tip 5 is also advantageously rounded in the axial direction, as can be seen in FIGS. 5 and 6.

Figure 3:
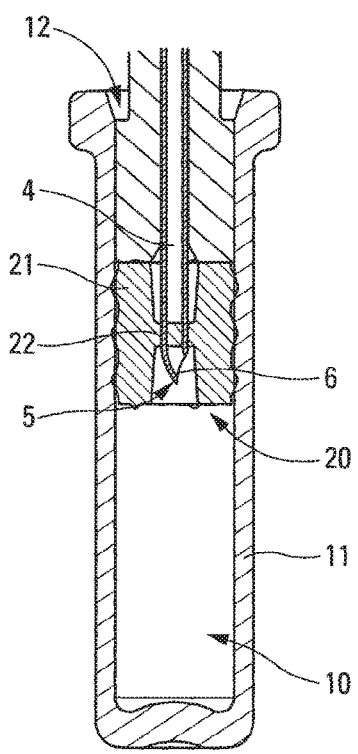
FIG. 3 is a view similar to the view in FIG. 2a, showing an advantageous embodiment of the present invention.
Figure 7:
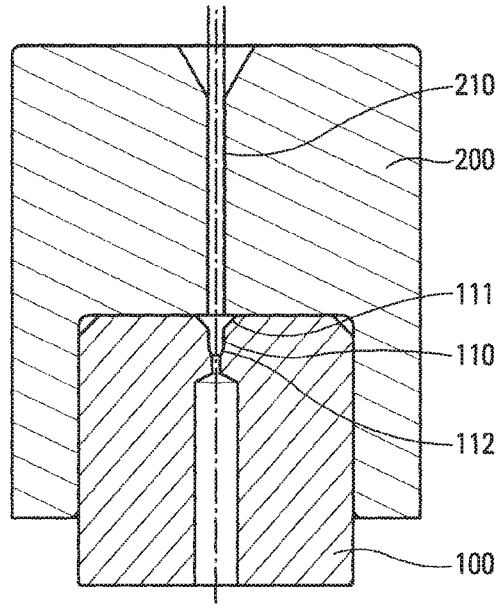
FIG. 7 is a diagrammatic view of an advantageous stamping unit for achieving the embodiment of FIGS. 3 to 6.

Advantageously, said perforating tip 5 is formed by stamping said cannula 4. FIG. 7 is a diagram showing a stamping unit, with a deformation bottom portion 100, and a guide top portion 200. The guide top portion 200 includes a cylindrical channel 210 for receiving the cannula 4, and the bottom portion 100 includes a deformation zone 110. The deformation zone advantageously includes an inlet portion 111 of diameter that is greater than the diameter of the cannula 4, and a deformation portion 112 of diameter that is smaller than the diameter of the cannula 4. When the tip of the cannula is forced into said deformation zone 110, it becomes deformed so as to form the tip shown in FIGS. 4 to 6. More precisely, in this embodiment, the end of the cannula 4 is deformed radially so as to bring the distal axial end 59 of the perforating tip onto the longitudinal central axis A. Since the deformation portion 112 is of small diameter, the peripheral edge 7 of the tip becomes deformed so as to generate said radial narrowing 7a in order to define the pear shape of the opening 6, with said distal portion 6a of small width. Advantageously, said deformation portion 112 is of rounded shape, which gives said tip its rounded profile towards its perforating end 59, as can be seen in FIGS. 3 and 4.

The present invention is described above with reference to an advantageous embodiment, but naturally any modification could be applied thereto by a person skilled in the art, without going beyond the ambit of the present invention, as defined by the accompanying claims.

The invention claimed is:

1. A fluid dispenser device comprising a body, and a dispenser head that is provided with a dispenser orifice and that is axially movable relative to said body during actuation, said body receiving a reservoir containing fluid, said reservoir comprising a hollow tube having a proximal axial opening that is closed by a stopper that is adapted to slide in leaktight manner in said tube during actuation, said dispenser head including a cannula including a perforating tip for perforating a perforating site, said perforating tip being provided with an opening, said opening defining a peripheral edge that extends around said opening and that includes a distal axial end and a proximal axial end, said distal axial end of said peripheral edge forming the distal axial end of the perforating tip, said distal axial end of the perforating tip being arranged on the longitudinal central axis of said cannula, wherein said perforating tip has an outer shape that is rounded in the radial direction, and said distal axial end of said perforating tip is of shape that is rounded in the axial direction.

2. A device according to claim 1, wherein said opening includes a distal portion of width that is small relative to the width of said cannula.

3. A device according to claim 2, wherein said peripheral edge includes a radial narrowing for defining said distal portion of small width of said opening.

4. A device according to claim 3, wherein said peripheral edge is curved axially.

5. A device according to claim 1, wherein said perforating tip is formed by stamping said cannula.

6. A device according to claim 1, wherein said cannula is connected at one end to said dispenser orifice, and it is provided at its other end with said perforating tip.

7. A device according to claim 1, wherein said reservoir is formed by a blind hollow tube.

8. A device according to claim 1, wherein said reservoir contains a single dose of fluid for dispensing during a single actuation of the device.

9. A device according to claim 1, wherein said reservoir contains two doses of fluid for dispensing during two successive actuations of the device.

* * * * *